United States Patent [19]

Aoki et al.

[11] Patent Number: 4,487,718

[45] Date of Patent: Dec. 11, 1984

[54] PEPTIDES

[75] Inventors: Nobuo Aoki, Utsunomiya; Taro Tamaki, Tokyo, both of Japan

[73] Assignee: Kowa Company, Ltd., Nagoya, Japan

[21] Appl. No.: 580,807

[22] Filed: Feb. 16, 1984

[30] Foreign Application Priority Data

Mar. 9, 1983 [JP] Japan .................................. 58-38564

[51] Int. Cl.³ ........................................... C07C 103/52
[52] U.S. Cl. ............................................. 260/112.5 R
[58] Field of Search ................................ 260/112.5 R

[56] References Cited

U.S. PATENT DOCUMENTS 4,434,095  2/1984  Chipens et al. .............. 260/112.5 R

*Primary Examiner*—Delbert R. Phillips
*Attorney, Agent, or Firm*—Oblon, Fisher, Spivak, McClelland & Maier

[57] ABSTRACT

A peptide of the formula:

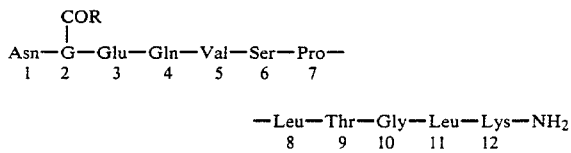

wherein G-COOH is Glu, and R is an amino or chromophore group is effective as a therapeutic drug for hemostatic disorders and thrombosis.

3 Claims, 5 Drawing Figures

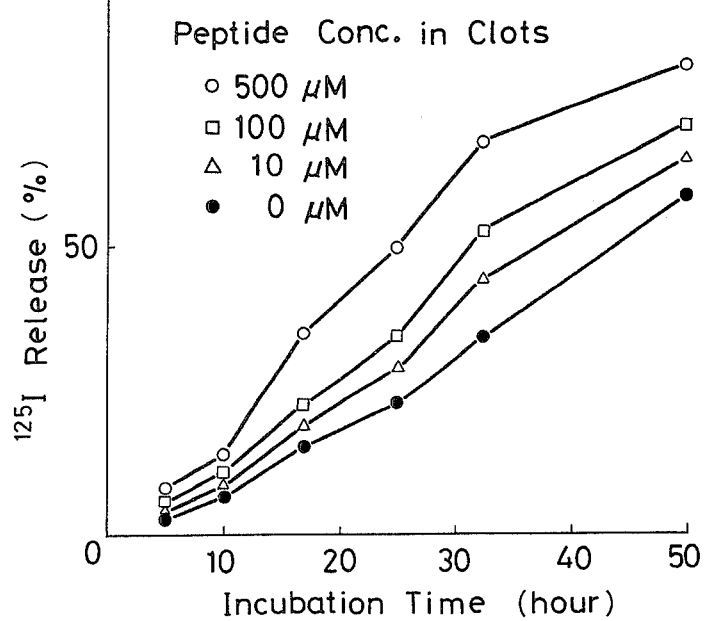
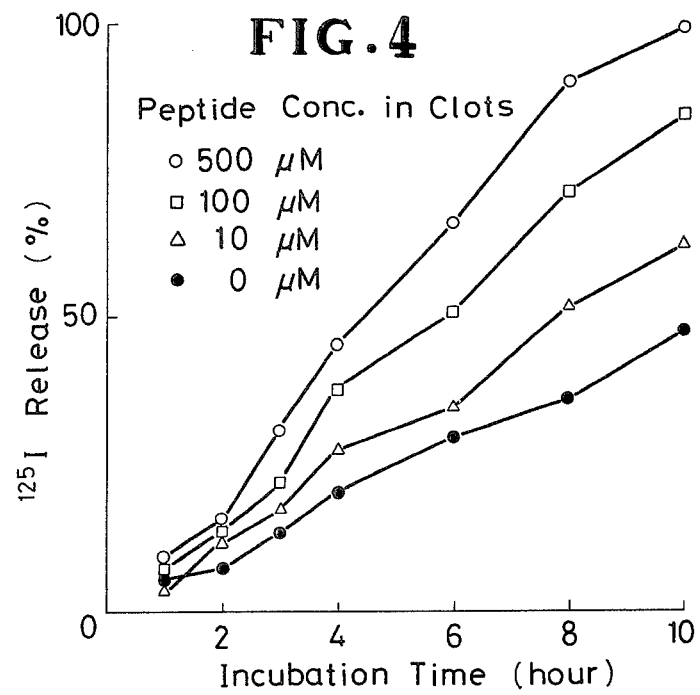

PEPTIDES

BACKGROUND OF THE INVENTION

1. Field of the Invention

This invention relates to novel peptides and more specifically to a peptide represented by the following formula (I):

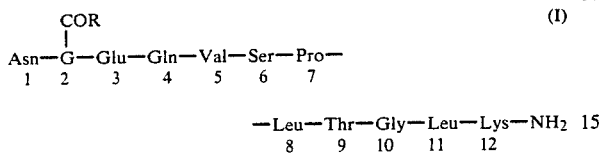

wherein G-COOH is Glu, and R is an amino or chromophore group.

The novel peptide of the formula (I) above has an inhibitory activity effect against the $\alpha_2$-plasmin inhibitor present in blood. Such compound is a good glutamine substrate for the activated blood coagulation factor XIII and hence is effectively useful as a medicine capable of exhibiting a fibrinolysis-accelerating effect and also as a diagnostic reagent for hemostatic disorders, thrombosis and the like.

2. Description of the Prior Art

The present inventors have previously isolated and purified an antifibrinolytic substance from human plasma and have named the substance "$\alpha_2$-plasmin inhibitor" (which may hereinafter be referred to simply as "$\alpha_2$-PI"). It has been reported by these inventors that $\alpha_2$-PI inhibits plasmin instantaneously and irreversibly and hence inhibits the binding of plasminogen with fibrin, resulting in suppressed activation of the plasminogen on the fibrin and impaired fibrinolysis [see "Prog. Cardiovasc. Dis.", 21, 267–286 (1979)].

It has also been confirmed that when blood coagulation takes place, $\alpha_2$-PI is crosslinked to the $\alpha$-chains of fibrin by the activated blood coagulation factor XIII (an activated fibrin-stabilizing factor), the $\alpha_2$-PI-coupled fibrin is more resistant to physiological fibrinolysis, and $\alpha_2$-PI when coupled with the fibrin serves to act as a glutamine substrate for such factor XIII.

The present inventors have carried out continuous research on substances having an inhibitory effect against the activity of $\alpha_2$-PI. Through research efforts leading to this invention, it has now been found that among peptides composed of amino acids having a structure similar to the N-terminal structure of $\alpha_2$-PI, some selected homologs are capable of inhibiting the activity of $\alpha_2$-PI.

SUMMARY OF THE INVENTION

Accordingly, this invention provides a peptide of the formula (I) which is of significant advantage as a medicine for fibrinolysis acceleration and also as a reagent for diagnosis of hemostatic disorders, thrombosis and the like.

A more specific object of the invention is to provide peptides represented respectively by the following formulae (Ia) and (Ib):

Asn—Gln—Glu—Gln—Val—Ser—Pro—    (Ia)
 1    2    3    4    5    6    7

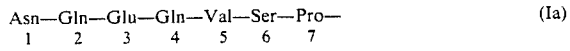

and

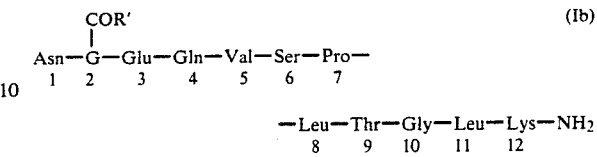

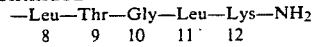

wherein R' is a chromophore group.

BRIEF DESCRIPTION OF THE DRAWINGS

A fuller understanding of this invention and many of the attendant advantages thereof will be had from the following detailed description when considered in connection with the accompanying drawings wherein:

FIG. 3 shows diagrammatically the fibrinolysis-accelerating effect of the peptide (Ia); and FIGS. 4 and 5 are diagrammatic illustrations of the synergistic effects accruing from the combined use of the peptide (Ia) and a tissue plasminogen activator.

DETAILED DESCRIPTION OF THE PREFERRED EMBODIMENTS

Figure 1:
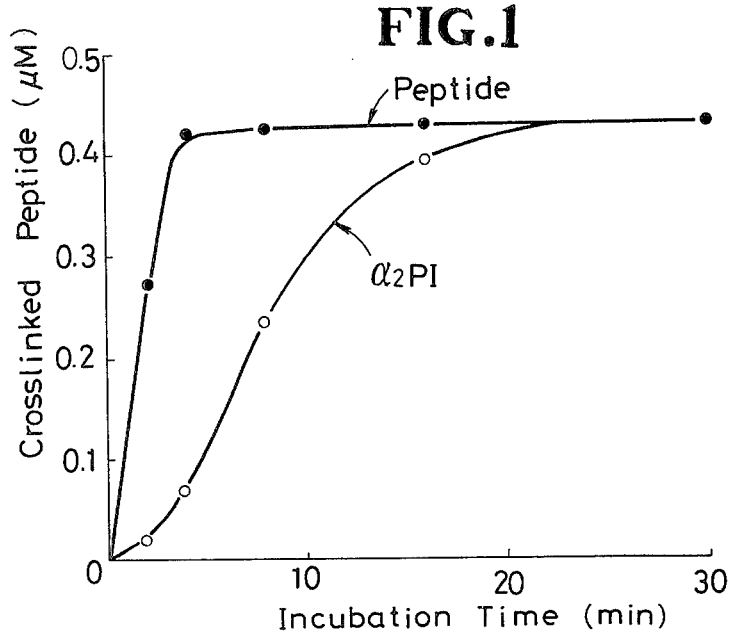
FIG. 1 is a diagram showing the crossliking capacity of a peptide (Ia) of the invention to fibrin.

A peptide of the formula (I) according to this invention may be prepared by a variety of processes which are employed commonly for peptide synthesis. Generally, a solid-phase or liquid-phase process may be used which makes it possible to apply, in combination, a successive coupling method of component amino acids, a fragment condensation method and the like.

Where component amino acids contain other functional groups, suitable protecting groups are used to protect these functional groups. Connection and subsequent removal methods of the protecting groups may be conducted by combining suitable procedures in various ways.

More specifically, the peptide (I) of the invention may be produced, for example, through successive condensation beginning with the lysine (No. 12) of the formula (I) by the solid-phase process using a polystyrenebenzhydrylamine resin.

As an $\alpha$-amino protecting group, use is made of a t-butyloxycarbonyl group. Eligible protecting groups for the functional groups of amino acids on their side chains may include an o-chlorobenzyloxycarbonyl group for the amino group, a benzyl group for the hydrozxl group, and a benzyl ester group for the carboxyl group.

As a releasing method of the peptide (I) from the resin, hydrogen fluoride may be used to treat the peptide-bearing resin at low temperatures. Thus, the peptide (I) is readily released and isolated from the resin.

The peptide (I) of the invention is in nature crosslinkable with fibrin in clots present in blood by the activated blood coagulation factor XIII and hence is competitively inhibitory against the crosslinking of $\alpha_2$-PI to the fibrin in the clots. Therefore, because of its fibrinolysis-accelerating effect, the peptide (I) can be satisfactorily used for pharmaceutical purposes, for example, as a therapeutic drug for thrombosis, either singly or in combination with other drugs.

Moreover, since the peptide (I) of the invention is a glutamine substrate susceptible to a specific reaction with the activated blood coagulation factor XIII, two compounds derived from the peptide (I) are effectively useful as diagnostic and analytical reagents. One of these compounds is a compound obtained by labeling a peptide of the formula (Ia) with a radioactive element, and the other is a peptide of the formula (Ib) containing a chromophore introduced in the γ-carboxyl group of glutamic acid indicated by the reference numeral 2 in the formula (Ib).

As an introduction method of the chromophore residual group, the various methods stated above may be applied by using a glutamic acid derivative in which a chromophore has in advance been introduced. Alternatively, such a chromophore may be introduced directly into the peptide (Ia).

Any chromophore residual groups may be used so long as they can be measured in the visible and/or ultraviolet ranges. Eligible examples are p-nitro aniline, aminomethylcoumarinic acid and the like.

This invention will now be described with reference to the following experimental examples and specific examples which are provided for purposes of illustration only and are not construed as limiting to the invention.

The activities and effects of the peptide (Ia) of the invention were tested with the results given below.

EXPERIMENT 1

Crosslinking capacity of the peptide (Ia) to fibrin:

To a mixed solution of 20 μl of the peptide (Ia) labeled with a radioactive isotope $^{125}I$, 20 μl of fibrinogen (30 mg/ml, 88 μM, containing 2 or 10 μ/ml of the blood coagulation factor XIII) and 140 μl of a Tris buffer, was added 20 μl of a mixed solution of thrombin (3.3 u/ml) and calcium chloride (50 mM). The resulting mixture was then incubated at 37° C.

The clotting sample was frozen instantaneously at each time with dry ice/acetone to terminate the reaction and then lyophilized. The resulting fibrin film was washed three times, each for 5 minutes, with 200 μl of 50 mM EDTA containing 1% of BSA (brovine serum albmin). The thus washed fibrin film was measured in its radioactivity to determine the amount of the peptide coupled with the fibrin [see "Biochim, Biophys, Acta", 661, 280–286, (1981)]. The results are shown in FIG. 1.

The peptide (Ia) of the invention was crosslinked promptly to the fibrin and reached the equilibrium when about 40% of the peptide (Ia) had been coupled. The crosslinking velocity of the peptide (Ia) was substantially the same as that of $\alpha_2$-PI.

It has thus been confirmed from these results that the peptide of the invention is a good glutamine substrate for the activated blood coagulation factor XIII.

EXPERIMENT 2

Inhibitory effect of the peptide (Ia) against the crosslinking of $\alpha_2$-PI to fibrin:

Twenty microliters of a mixed solution of thrombin (3.3 u/ml) and calcium chloride (50 mM) was added to a mixed solution consisting of 20 μl of fibrinogen (30 mg/ml, 88 μM, containing 10 u/ml of the blood coagulation factor XIII), 20 μl of $\alpha_2$-PI (0.67 mg/ml, 10 μM), 20 μl of a $^{125}I$-labeled peptide (0–50 mM) and 120 μl of a Tris buffer. The amount of the peptide bonded to the resulting fibrin clot was then determined in the same manner as in Experiment 1.

Figure 2:
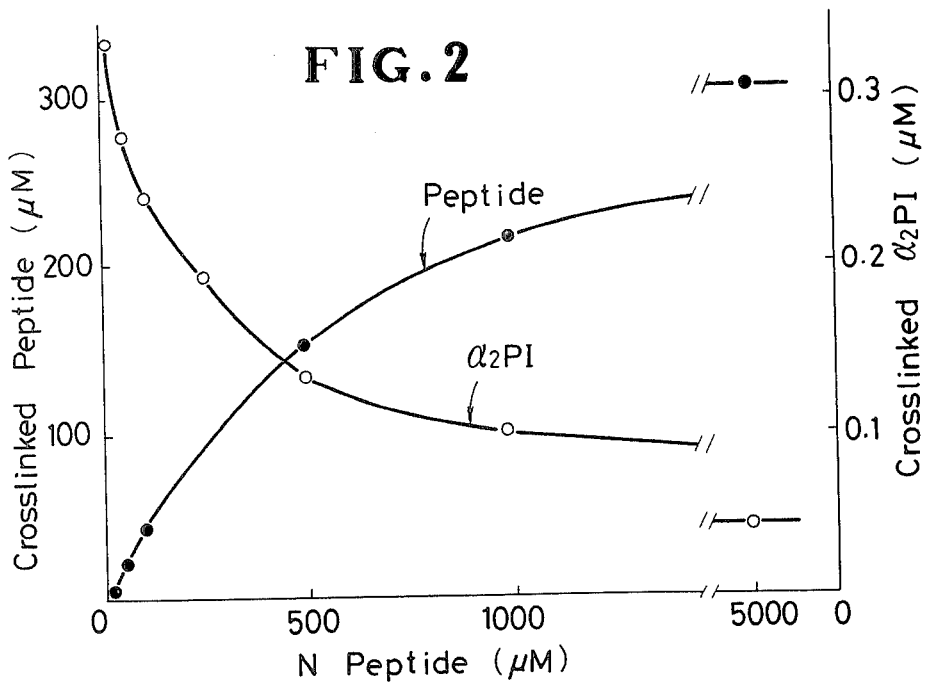
FIG. 2 shows diagrammatically the inhibitory effect of the peptide (Ia) against the crosslinking of $\alpha_2$-PI to fibrin.

On the other hand, the amount of $\alpha_2$-PI coupled with a fibrin clot was also determined using $^{125}I$-labeled $\alpha_2$-PI and an unlabeled peptide. The results are shown in FIG. 2.

From the above results, it is understood that the peptide of the invention inhibits competitively the crosslinking of $\alpha_2$-PI to the fibrin.

EXPERIMENT 3

Fibrinolysis-accelerating effect of the peptide (Ia):

Healthy human blood to which sodium citrate had been added, was subjected to centrifugal separation to prepare platelet-rich plasma. A trace amount of $^{125}I$-labeled fibrinogen was added to and mixed with the platelet-rich plasma. 250 mM solutions of calcium chloride which contained the peptide (Ia) at different levels (0–5 mM) were poured, each in a volume of 20 μl, into glass test tubes. Each test tube was added with 180 μl of the above plasma and then allowed to stand at 37° C. A fibrin clot was formed in several minutes. Clot retraction started about 15 minutes later and was completed in about 30 minutes.

Thereafter, 800 μl of platelet-poor plasma which contained the peptide (Ia) at different levels (0–500 μM) and 1 u of Hirudin was added to each of the test tubes. The test tube was then incubated at 37° C. The contents were sampled periodically to measure $^{125}I$ released into the supernatant. The results are shown in FIG. 3.

It is envisaged that the peptide (Ia) of the invention has a fibrinolysis-accelerating effect because the dissolution of each fibrin clot is promoted by addition of the peptide (Ia), as compared with the case where the peptide (Ia) is absent and that such effect is proportional to the amounts of the peptide (Ia) added.

EXPERIMENT 4

Synergistic effects of the peptide (Ia) used in combination with a plasminogen activator:

(1) Addition of the peptide (Ia) and the activator before clot formation:

Healthy human blood to which sodium citrate had been added, was subjected to centrifugal separation to prepare platelet-rich plasma. A trace amount of $^{125}I$-labeled fibrinogen was added to and mixed with the platelet-rich plasma. 250 mM solutions of calcium chloride which contained the peptide (Ia) at different levels (0–5 mM) and 1 u/ml of a melanoma-derived tissue plasminogen activator (TPA), were poured 20 μl by 20 μl into glass test tubes, each of which was then added with 180 μl of the above plasma. A fibrin clot was formed in several minutes. Clot retraction started about 15 minutes later and was completed in about 30 minutes.

Thereafter, each test tube was added with 800 μl of platelet-poor plasma which contained the peptide (Ia) at different levels (0–500 μM) and 1 u of Hirudin. The test tube was then incubated at 37° C. The contents were sampled periodically to measure $^{125}I$ released into the supernatant. The results are shown in FIG. 4.

(2) Addition of the peptide (Ia) and the activator after completion of clot formation:

Healthy human blood to which sodium citrate had been added, was subjected to centrifugal separation to prepare platelet-rich plasma. A trace amount of $^{125}I$-labeled fibrinogen was added to and mixed with the platelet-rich plasma. 250 mM solutions of calcium chloride were poured 20 μl by 20 μl into glass test tubes, each of which was then added with 180 μl of the above plasma. A fibrin clot was formed in several minutes. Clot retraction started about 15 minutes later and was completed in about 30 minutes.

Figure 5:
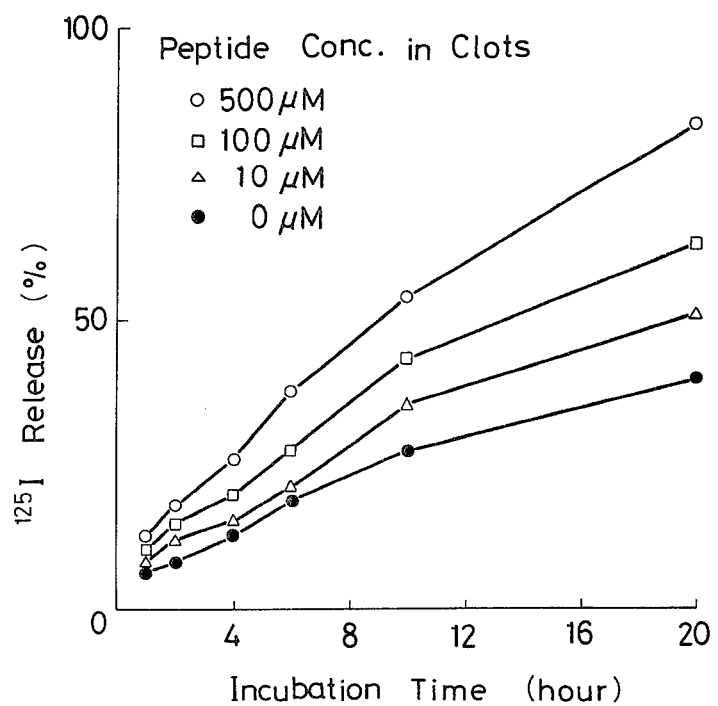

Thereafter, each test tube was added with 800 μl of platelet-poor plasma which contained the peptide (Ia) at different levels (0–500 μM) and 1 u of Hirudin and 1.25 u of a melanoma-derived tissue plasminogen activator (TPA). The test tube was then incubated at 37° C. The contents were sampled periodically to measure $^{125}I$ released into the supernatant. The results are shown in FIG. 5.

It is understood that when used in combination with a plasminogen activator, the peptide (Ia) of the invention brings about a synergistically enhanced fibrinolysis-accelerating effect because such effect is substantially increased by adding the tissue plasminogen activator to the peptide (Ia), as compared with the case where no such activator is added.

EXAMPLE 1

(1) In a manual solid-phase synthesis reactor was placed 1.64 g of a benzhydrylamine resin hydrochloride (which contained 1.0 mmol of amino groups). After being neutralized with a 5% solution of diisopropylethylamine in methylene chloride, the hydrochloride was successively condensed, beginning with the carboxyl-terminated amino acid, by a solid-phase synthesis reaction.

The following amino acids were used after introducing protecting groups wherever needed.

| | | |
|---|---|---|
| (1) | Boc—L-Lys(o-ClZ) t-But$^N$H$_2$ (used after removal of t-ButNH$_2$) | 1.63 g |
| (2) | Boc—L-Leu H$_2$O (used after dehydration) | 0.75 g |
| (3) | Boc—L-Gly | 0.53 g |
| (4) | Boc—L-Thr(Bzl) | 0.93 g |
| (5) | Boc—L-Pro | 0.65 g |
| (6) | Boc—L-Ser(Bzl) | 0.89 g |
| (7) | Boc—L-Val | 0.65 g |
| (8) | Boc—L-Gln | 0.74 g |
| (9) | Boc—L-Glu(OBzl) | 1.01 g |
| (10) | Boc—L-Asn | 0.70 g | o-ClZ: o-chlorobenzyloxycarbonyl
Bzl: benzyl
OBzl: benzyl ester

The removal of the t-butyloxycarbonyl group (Boc) was effected by treating each amino acid with a 50% solution of trifluoroacetic acid in methylene chloride at room temperature for 30 minutes.

The neutralization of trifluoroacetic acid was effected by treating the resulting solution with a 5% solution of diisopropylethylamine in methylene chloride for 10 minutes.

The extension of the peptide chain was effected by reacting 3 equivalents of the Boc-amino acid with a methylene chloride solution of dicyclohexylcarbodiimide at room temperature for 3 hours. N-Hydroxybenzotriazole was added when condensing glutamine and asparagine.

Any excess reagent or reagents in each reaction were removed by washing with methylene chloride, dimethylformamide, isopropyl alcohol or the like.

By the above-mentioned treatments, 3.3 g of a resin was obtained which contained a peptide having the following amino acid composition.

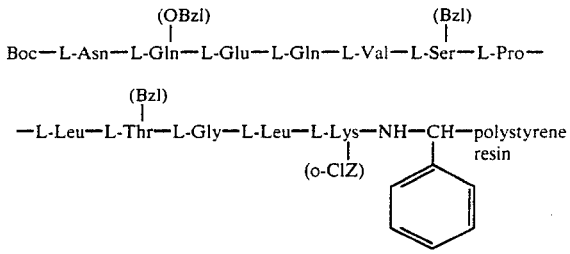

(2) In an anhydrous hydrogen fluoride reactor was placed 2.0 g of the peptide-containing resin obtained in item (1) above. The resin was added with 2 ml of anisole and then with 20 ml of hydrogen fluoride. The resulting mixture was reacted at 0° C. for 60 minutes.

Excess hydrogen fluoride was evaporated under reduced pressure, and the residue was dissolved in distilled water. The resulting solution was caused to pass through a column packed with Dowex X-1 (an acetic acid type, trademark, Dow Chemical Co.), and the effluent was collected and then lyophilized to obtain 623 mg of a crude product. The crude product was dissolved in distilled water and then subjected to reverse phase high-performance liquid chromatography using an acetonitrile-phosphoric acid buffer as an eluant. The main peak was collected. Acetonitrile was removed under reduced pressure, and the resulting solution was again caused to pass through a column packed with Dowex X-1 (an acetic acid type). The effluent was desalted and then lyophilized to obtain 130 mg of the following intended peptide.

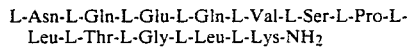

Appearance: Colorless powder
Rotary power: $[\alpha]_D^{32} - 96.5°$ (c 0.26, H$_2$O).
Elemental analysis: Calculated for C$_{56}$H$_{97}$N$_{17}$O$_{19}$ CH$_3$COOH 10H$_2$O: C,44.86; H, 7.86; N, 15.34 Found: C,44.87; H, 7.24; N, 15.67.
Amino acid analysis: 6N HCl, 110° C., 42-hour phenol treatment: Lys(1) 1.02, NH$_3$(4) 5.20, Asp(1) 0.98, Thr(1) 0.95, Ser(1) 0.87, Glu(3) 2.91, Pro(1) 1.01, Gly(1) 1.00, Val(1) 0.99, Leu(2) 1.98.
Silica gel thin-layer chromatography: Developing solvent (n-butyl alcohol: acetic acid: water: pyridine = 15:3:12:10) (%). R$_f$ value: 0.55 (single spot).

EXAMPLE 2

The procedure of Example 1 was repeated, except that

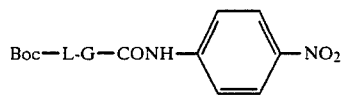

was used in place of Boc-L-Gln, to obtain the following compound.

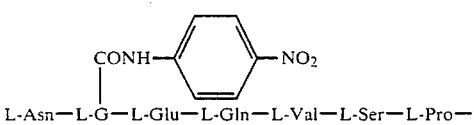

—L-Leu—L-Thr—L-Gly—L-Leu—L-Lys—NH₂

Having thus described this invention, it will be apparent to one having ordinary skill in the art that many changes and modifications may be made thereto without departing from the spirit or scope of the invention as set out in the appended claims.

What is claimed is:

1. A peptide of the following formula (I):

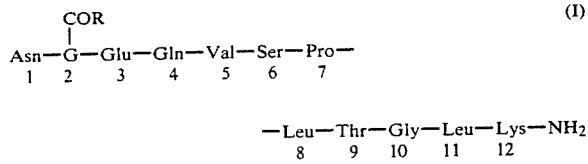

(I)

wherein G-COOH is Glu, and R is an amino or chromophore group.

2. A peptide of claim 1 having the following formula (Ia):

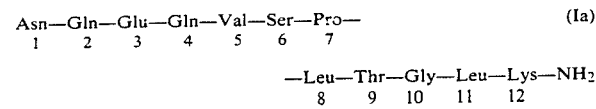

(Ia)

3. A peptide of claim 1 having the following formula (Ib):

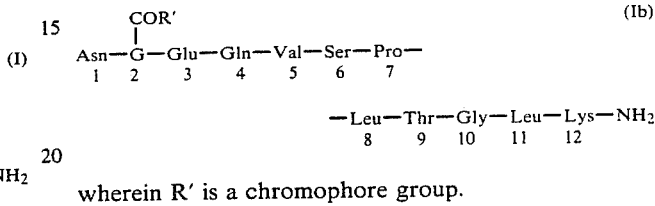

(Ib)

wherein R' is a chromophore group.

* * * * *